United States Patent
Beyerer et al.

(10) Patent No.: US 6,873,721 B1
(45) Date of Patent: Mar. 29, 2005

(54) METHOD AND DEVICE FOR DETERMINING AN ANGLED STRUCTURE IN THE SURFACE OF A PRECISION MACHINED CYLINDRICAL WORK PIECE

(75) Inventors: Jürgen Beyerer, Dielheim (DE); Doris Krahe, Karlsruhe (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/623,962

(22) PCT Filed: Mar. 5, 1999

(86) PCT No.: PCT/EP99/01442

§ 371 (c)(1),
(2), (4) Date: Feb. 22, 2001

(87) PCT Pub. No.: WO99/46583

PCT Pub. Date: Sep. 16, 1999

(30) Foreign Application Priority Data

Mar. 9, 1998 (DE) ........................ 198 09 790

(51) Int. Cl.$^7$ ................................ G06K 7/00
(52) U.S. Cl. ................ 382/152; 382/248; 382/260; 382/278; 378/15; 378/901; 348/88
(58) Field of Search ................ 382/108, 152, 382/248, 255, 278, 280, 294, 312, 131, 260; 356/430, 606, 237.2; 250/559.46, 201.3; 348/88, 90; 378/4, 15, 17, 901

(56) References Cited

U.S. PATENT DOCUMENTS

| | | | |
|---|---|---|---|
| 4,162,126 A | * | 7/1979 | Nakagawa et al. ...... 356/237.2 |
| 4,760,563 A | * | 7/1988 | Beylkin ........................ 367/73 |
| 5,245,409 A | | 9/1993 | Tobar et al. |
| 5,390,112 A | * | 2/1995 | Tam .............................. 378/17 |
| 5,463,666 A | * | 10/1995 | Eberhard et al. ............... 378/4 |
| 5,504,792 A | * | 4/1996 | Tam .............................. 378/15 |
| 5,537,210 A | * | 7/1996 | Kaneda et al. ............... 356/499 |
| 5,680,484 A | | 10/1997 | Kikuchi et al. |
| 5,901,196 A | * | 5/1999 | Sauer et al. ..................... 378/4 |

FOREIGN PATENT DOCUMENTS

| | | |
|---|---|---|
| DE | 197 40 141 | 4/1999 |
| EP | 0 358 982 | 3/1990 |
| GB | 2 126 712 | 3/1984 |
| WO | WO 97 00438 | 1/1997 |
| WO | WO 97 46969 | 12/1997 |

OTHER PUBLICATIONS

G. Kersten, "Optische und antastende Prüfung der Gegenlauffläche von Radial–Vellendichtringen" [Optical an contact testing of the mating bearing surface of radial shaft sealing rings], VDI Verlag, Dusseldorf, 1992, vol. 281, p. 103+.

* cited by examiner

*Primary Examiner*—Bhavesh M. Mehta
*Assistant Examiner*—Sheela Chawan
(74) *Attorney, Agent, or Firm*—Kenyon & Kenyon

(57) ABSTRACT

A method for determining a helical groove structure, for example in the form of flutes, in the surface of a finely finished cylindrical workpiece, in particular the ground mating bearing surface of radial shaft sealing rings, which is characterized in that a camera is used to record at least one image of the illuminated surface of the workpiece, which image reproduces the helical groove structure in the surface of the workpiece. A device for carrying out a method includes a CCD camera with a macrolens, a radial bearing device for the workpiece, an illuminating device and an image reading and image processing device.

14 Claims, 7 Drawing Sheets

METHOD AND DEVICE FOR DETERMINING AN ANGLED STRUCTURE IN THE SURFACE OF A PRECISION MACHINED CYLINDRICAL WORK PIECE

FIELD OF THE INVENTION

The present invention relates to a method for determining the structure of machining marks on the surface of a cylindrically finely finished workpiece with the aid of a camera, the camera and the workpiece being mutually aligned, and an image of the surface characteristics of the workpiece being recorded.

BACKGROUND INFORMATION

The so-called light-scattering method provides the basis as prior art. This generally known technique is described in European Published Patent Application No. 358 982, British Published Patent Application No. 2 126 712 or U.S. Pat. No. 4,162,126.

For a reliable sealing function at points where shafts pass through housing walls, it is necessary also to take into account not only the sealing ring provided with an annular radial sealing lip but also the properties of the mating bearing surface on the shaft side. It usually comprises circumferentially ground shaft journal surfaces. Other possibilities of fine finishing are burnishing, roller-burnishing, external rubbing and high-precision cutting. The design engineer prescribes that the ground structure of the shaft journal should not only have specific roughness values but also be free from helical grooves. Freedom from helical grooves means that the ground structure lies exactly in the circumferential direction and there are no superimposed regular portions of the shaft.

Until now, it has largely been assumed that the so-called plunge-cut grinding method produces structures which are free from helical grooves. However, even with the unreliable so-called thread method—more details on this below—it is possible to prove that, at least with a certain combination of working parameters, even when the plunge-cut grinding method is used, helical groove structures may be produced on the workpiece surface which has been finely finished in this way.

The radial sealing lip of a sealing ring bears with a rubber-elastic sealing edge against the surface of the shaft journal with a defined radial force and over a specific axial width. As a result of the rotation of the shaft journal, the bearing region of the sealing lip is deformed to different degrees in the circumferential direction as a function of the local radial bearing pressure; smaller degrees of deformation are found near the edge and relatively severe circumferential deformations are found more in the centre region of the bearing strip. This leads to a sensitive tribological and rheological equilibrium with an oil flow which ensures the lubrication of the contact zone on the one hand, and a feedback mechanism which maintains the sealing function of the annular seal, on the other. This equilibrium must not be disrupted by a helical groove phenomenon in the microstructure of the mating bearing surface. A feeding action in one or the other direction, due to a helical groove, is to be avoided. In the case of a feeding effect, due to a helical groove, into the sealed interior of the housing, the seal would run dry, external contamination would be fed into the contact zone and the seal would wear prematurely and be broken. An outwardly directed feeding effect would prevent the seal running dry but would lead to an oil leak at the sealing point, which, for different reasons, must be more or less strictly avoided.

Apart from standarized methods according to DIN 3761, Part 2, Section 5.1.4 (see further below for more details), these properties have in the past also been monitored using the so-called thread method, but this method provided only very unreliable information, which, however, was frequently not noted at all. The thread method is a non-standardized method, which is therefore less widespread in the literature and is described, for example, incidentally, in German Patent No. 197 40 141 (not a prior publication) of the applicant and may also be referenced here once again. A method called a thread indicator is mentioned briefly, on page 103, in Volume No. 281 of the series of VDI progress reports on production engineering by G. Kersten "Optische und antastende Prüfung der Gegenlaufflache von Radial Wellendichtringen" ["Optical and contact testing of the mating bearing surface of radial shaft sealing rings"], VDI Verlag, D üsseldorf 1992. In the thread method, an oil-steeped thread, defined in terms of structure, material and strength, is wrapped somewhat more than 180° around the top of the horizontally aligned shaft journal; the ends which hang down are both attached to a small weight and the thread is thus loaded in a defined way. The shaft is then rotated slowly 20 times in one direction of rotation and then 20 times in the other direction. The axial displacement path of the thread on the surface of the journal is evaluated as a measure of the helical groove structure. The thread method supplies a clear measurement result. However, comparative measurements of the applicant using the thread method, on the one hand, and the present invention, on the other, have shown that the measurement results acquired with the thread method are in no way representative of the actual helical groove structure of the surface of the journal. The measurement results which can be obtained with the thread method do not in any way correlate with the observable tightness results or service lives of installed radial shaft sealing rings either.

It has proved to be particularly disadvantageous in the case of-the thread method that the thread itself can be affected by helical grooves, and this can lead to false, results. In addition, quantitative statements on the helical groove structure are impossible. Moreover, the thread method fails in the case of weak helical groove phenomena.

In accordance with DIN 3761, Part 2, Section 5.1.4, freedom from helical grooves, or the helical groove orientation can be established using the following method:

rotating the shaft under the microscope, taking of fax film impressions, and surface records transverse to the machining direction and at a plurality of points on the shaft circumference.

According to this DIN standard, whether a helical groove orientation is disadvantageous can be established only by means of a test run with a change in direction of rotation. However, as with the thread method, quantitative statements are likewise impossible using the method described in DIN 3761, Part 2, Section 5.1.4. Moreover, the method according to this DIN standard requires an experienced observer and lasts a long time. The hardware required for carrying out the method is complicated and expensive.

A complicated method, operating according to the segmental scanning principle, for determining a helical groove structure is described in German Patent No. 197 40 141 of the applicant (not a prior publication) already mentioned. This method provides reliable data on all individual parameters of a helical groove structure, in particular the number of threads, helix angle, helical groove depth and feed cross section—of a helical groove structure. However, the known method, operating according to the segmental scanning principle for determining a helical groove structure presupposes a high outlay on apparatus and much attention to staff and, over and above this, is very time-consuming to carry out. The known method for determining helical grooves can therefore be used at most as a scientific basic or reference method, but not as a monitoring method which is close to being capable of use in production.

The parameters of interest for a helical groove structure are explained in German Patent No. 197 40 141 mentioned with the aid of graphical illustrations of the helical groove structure, for which reason this specification is also helpful in understanding the terms used in the present application. It should be mentioned at this juncture that the term "flute" used in the present application is to be understood in the sense of the term "corrugation trough of the helical groove structure" used in German Patent No. 197 40 141. The helical groove structure of interest here is caused at least indirectly by a grinding operation. This is a periodic, thread-type, multi-start fine structure, on which a stochastic, even finer ground structure is superimposed. in this case, corrugation peaks oriented largely in the circumferential direction and of approximately the same cross-sectional form are equidistantly adjacent and extend in thread-type fashion around the workpiece circumference. The characteristics of the periodic shape component of a helical groove structure are defined as follows in German Patent No. 197 40 141:

The periodic length of a helical groove structure is the spacing, measured in the axial direction, of neighbouring corrugation peaks.

The number of threads of a helical groove structure is determined, from the number of the corrugation peaks along the circumferential direction over the complete shaft circumference. Thread numbers to far above 100 have been observed on real workpieces.

The helix lead is equal to a multiple of the periodic length which corresponds to the number of threads.

The helix angle (which is, as a rule, a small angle far below 5°, mostly in the range of minutes) is yielded— in circular measure—from the ratio of the circumferential length to the lead height. By trigonometric conversion, it is at least possible to use this ratio value to specify the helix angle in angular degrees, as well.

The profile depth or helical groove depth of a helical groove is the depth between two neighbouring corrugation peaks.

The open feed cross section seen in an axially extending section, between two neighbouring corrugation peaks can be measured by planimeter in accordance with the helical groove representation obtained using the segmented scanning method, or can be determined by calculation, assuming a sinusoidal form of the corrugation peak flanks, from the profile depth and the spacing of the corrugation peaks. When determining the area, it is also possible to take account of round shapes or pointed shapes of the corrugation peaks by means of appropriately extended evaluation software.

SUMMARY OF THE INVENTION

An object of the present invention is to specify a method for determining a helical groove structure in the surface of a finely finished cylindrical workpiece which permits qualitatively and quantitatively reliable statements on the formation and degree of salience of the helical groove structure. The aim in this case is to lend prominence to the speed of the method, the cost-effective implementation and the simple handling of the device.

Starting from a method for determining the structure of machining marks on the surface of a cylindrical finely finished workpiece with the aid of a camera, the camera and the workpiece being aligned with one another, and an image of the surface characteristics of the workpiece being recorded, the basic object is achieved according to the present invention by virtue of the fact that for the purpose of determining a helically running structure of machining marks a Radon transformation of the image is carried out and the helix angle of the helical machining marks is determined from the Radon transform.

This permits contactless detection and quantitative recording of helical groove phenomena, for example on ground mating bearing surfaces of radial shaft sealing rings. The method is suitable for use in the mass production of cylindrical workpieces. It permits the selection of the best parts from a finished series in production.

The use of a fast image processing algorithm permits a substantially quicker detection and quantification of helical grooves than is possible in the case of a sampling system. The use of image series renders the calculation of helix angles independent of adjustment, and thereby facilitates the handling of the measuring system used. A further advantage is to be seen in that standard components can be used to carry out the method according to the present invention. This ensures a cost-effective implementation when constructing the measuring system.

In the case of a device for carrying out the method according to the present invention, provision is made of a CCD camera with a macrolens, a radial bearing device for the workpiece, an illuminating device and an image reading and image processing device. The CCD camera is mounted on a macroscope for the purpose of recording grey-scale images of the workpiece surface. The illuminating device permits surface images to be recorded with a reproducible illuminating situation. A high contrast between flute peaks and troughs is generated with the aid of illumination which is incident in a very flat fashion.

It is possible to proceed in the following way when carrying out the present invention specifically when a single image suffices for detecting the surface structure:

a) The camera, and the workpiece are mutually aligned by adjusting the camera and the workpiece at a defined angle relative to one another. A high contrast is generated between flute peaks and troughs with the aid of illumination which is incident in a very flat fashion. The image section should be chosen such that between 5 and 50 flutes are to be seen. Fewer flutes limit the statistical reliability and reproducibility of the result, while more reduce the achievable resolution.

b) An image of the surface characteristics of the workpiece is recorded. Enlarged grey-scale images of the grinding texture can be recorded, for example, via a macrolens and a CCD camera. It suffices to record a single image of the surface for helix angles in the range of degrees.

c) A Radon transformation of the image is carried out. The Radon transformation is a method which effectively visualizes linear structures in images—The angular position of the flutes in the image is determined with the aid of the Radon transform of the image. The angle obtained from the Radon transform is, however, not yet the desired helix angle.

d) The helix angle is determined from the Radon transform. The difference between the angle defined in step a) and the angle determined in step c) is the desired helix angle. This method is particularly suitable for large helix angles in the range of degrees.

It is possible to proceed in the following way in an expedient refinement of the method according to the present invention, this mode of procedure being indicated when a plurality of images are required for the data-reliable detection of the surface structure:
a) The workpiece is set rotating. Theoretically, it is also possible to set the camera rotating around the workpiece, but it is simpler to set the workpiece rotating. This can be performed, for example, with the aid of a suitable drive by means of appropriately mounting the workpiece.
b) A plurality of images of the surface characteristics of the workpiece are recorded at a constant twisting angle. For relatively small helix angles of the magnitude of a few minutes, it is not sufficient to process only one image. In order to be able to measure small helix angles with a higher accuracy, plurality of images of the surface are recorded, affected by helical grooves, at a defined twisting angle (that is to say, a fixed image spacing in the circumferential direction).
c) The Radon transformation to be carried out is carried out for each image and a so-called Radon strip is extracted in each case therefrom. The periodic power component is calculated as the ratio of the proportion of the machining marks to the surface under consideration. Each flute is projected, by means of a Radon transformation carried out for each image, onto a region about local maximum, to be precise all parallel flutes of an image are projected,onto a strip via a fixed angle. The flutes appear in the image at the fixed angle with different spacings from the origin.
d) The Radon strips of the Radon transforms of each image are juxtaposed in a so-called Radon strip image. The region (Radon strip) of interest of each transform is extracted, and these Radon strips are assembled in an image. The helix angle is present enlarged in the Radon strip image thus produced, and can therefore be measured more accurately.
e) A correlation analysis of the juxtaposed Radon strips is carried out. The helix angle can be determined very reliably, accurately and independently of adjustment owing to the correlation of the Radon strips.

The expedient refinement, of the present invention just explained is characterized as follows:
a) the workpiece is set rotating,
b) a plurality of images of the surface characteristics of the workpiece are recorded at a constant twisting angle,
c) the Radon transformation to be carried out is carried out for each image and a so-called Radon strip is extracted in each case therefrom,
d) the Radon strip of the Radon transforms of each image are juxtaposed in a so-called Radon strip image, and
e) a correlation analysis of the juxtaposed Radon strips is carried but.

A further refinement, derived therefrom, of the present invention can be implemented in the following way:
a) A periodogram is formed from the Fourier transform. The periodogram is formed from the square of the absolute value of the Fourier transform. The periodogram serves as estimator for the power density spectrum.
b) The periodogram is multiplied by a comb filter. The periodic power component is extracted from the periodogram with the aid of the comb filter. The angular parameter of the comb filter can be determined, for example, with the aid of the above-described method for large angles. The spacing parameter of the comb filter is determined in conjunction with maximizing the periodic power component.
c) A Fourier transform of an image is produced. In order in addition to the angle also to make a quantative statement on the degree of salience of the helical groove, the ratio of the helical groove component to the total power of the flute texture is calculated. Since the helical flutes are periodic, the information contained therein is concentrated by the Fourier transformation onto points on a line perpendicular to the position in the texture image.
d) The optimized spacing parameter is an estimated value of the periodic length, likewise used as a variable describing helical grooves, of the helical groove structure.
e) The number of threads, a further parameter of the helical groove structure, can be calculated from the variables of helix angle and periodic length.

The expedient refinement of the present invention just explained is characterized in the following way:
a) in addition to the radon transform, a Fourier transform of an image is produced and a periodogram is formed therefrom,
b) the periodogram is filtered using a comb filter, the spacing parameter of the comb filter being determined in conjunction with maximization of the periodic power component,
c) the periodic power component is calculated as the ratio of the proportion of the machining marks to the surface under consideration,
d) the spacing parameter of the comb filter is used as estimated value of the periodic length of the helical groove structure, and
e) the number of threads of the helical groove structure is calculated from the variables of helix angle and periodic length.

In a further expedient refinement of the present invention, it can be provided that a scale is provided at the level of the workpiece surface. Determining the spacing between successive images, and converting this spacing into a number of pixels are decisive for the accuracy of the helix angle calculation. A simple way for determining this spacing has been found within the framework of the present invention. A material measure, for example millimetre-square graph paper, is fastened on the specimen, and a grey-scale image is recorded at the desired enlargement. The spacing of the millimetre lines can be determined in pixels with the aid of the Radon transform, and converted directly into a constant.

Further advantages, features and details of the present invention, emerge from the following description, in which an exemplary embodiment is described in detail reference to the drawings. In this case, the features described in the specification can respectively be used in individually per se or in any combination.

DETAILED DESCRIPTION

Figure 1:
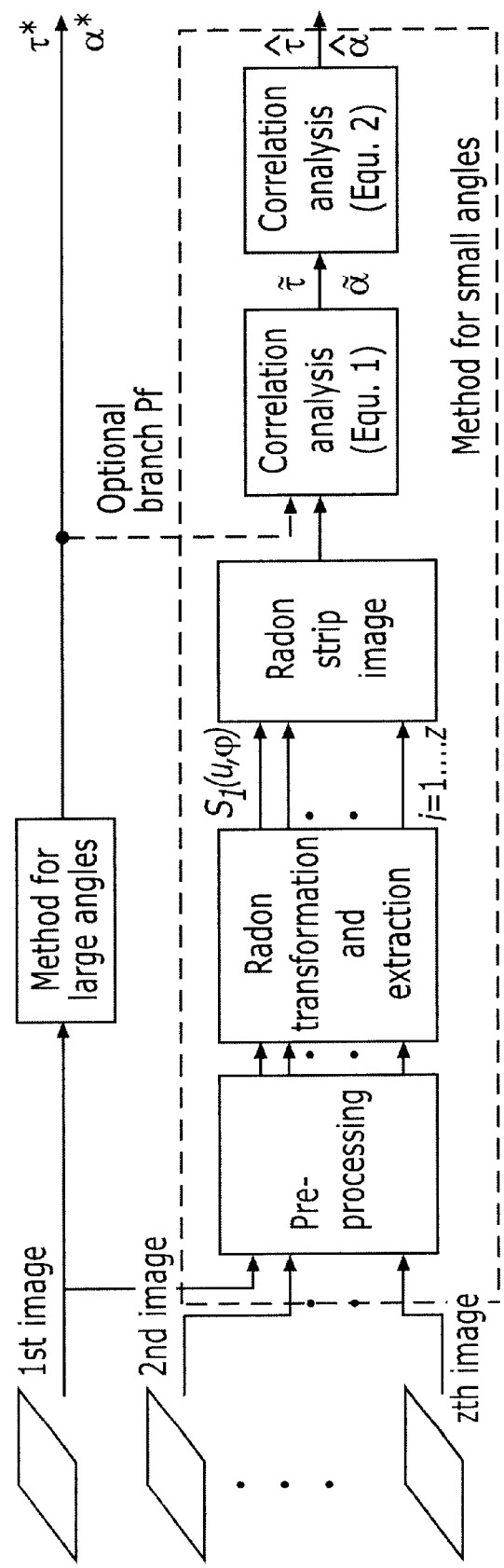
FIG. 1 shows a schematic illustration of the sequence of the method according to the present invention.

FIG. 1 shows a schematic illustration of the sequence of the method according to the present invention for estimating the helix angle. Enlarged grey-scale images of the grinding texture of a shaft mounted in a horizontally rotatable fashion are recorded via a macrolens and a CCD camera. Large helix angles a in the range of degrees can be estimated from a single image of the surface by adjusting the camera and the workpiece at a defined angle g relative to one another and determining the angular position of the flutes in the image by means of a Radon transform of the image. The difference between the defined and measured angles is the elix angle.

The Radon transformation R is a method which effectively visualizes linear structures in images:

$$R\{g(\vec{x})\} = \breve{g}(u, \varphi) = \iint_{Bild} g(\vec{x}) \delta(\vec{x}^T \vec{e}_\varphi - u) d\vec{x} = \iint_{Bild} g(\vec{x}) \delta(x\cos\varphi + y\sin\varphi - u) dx dy$$

Figure 2:
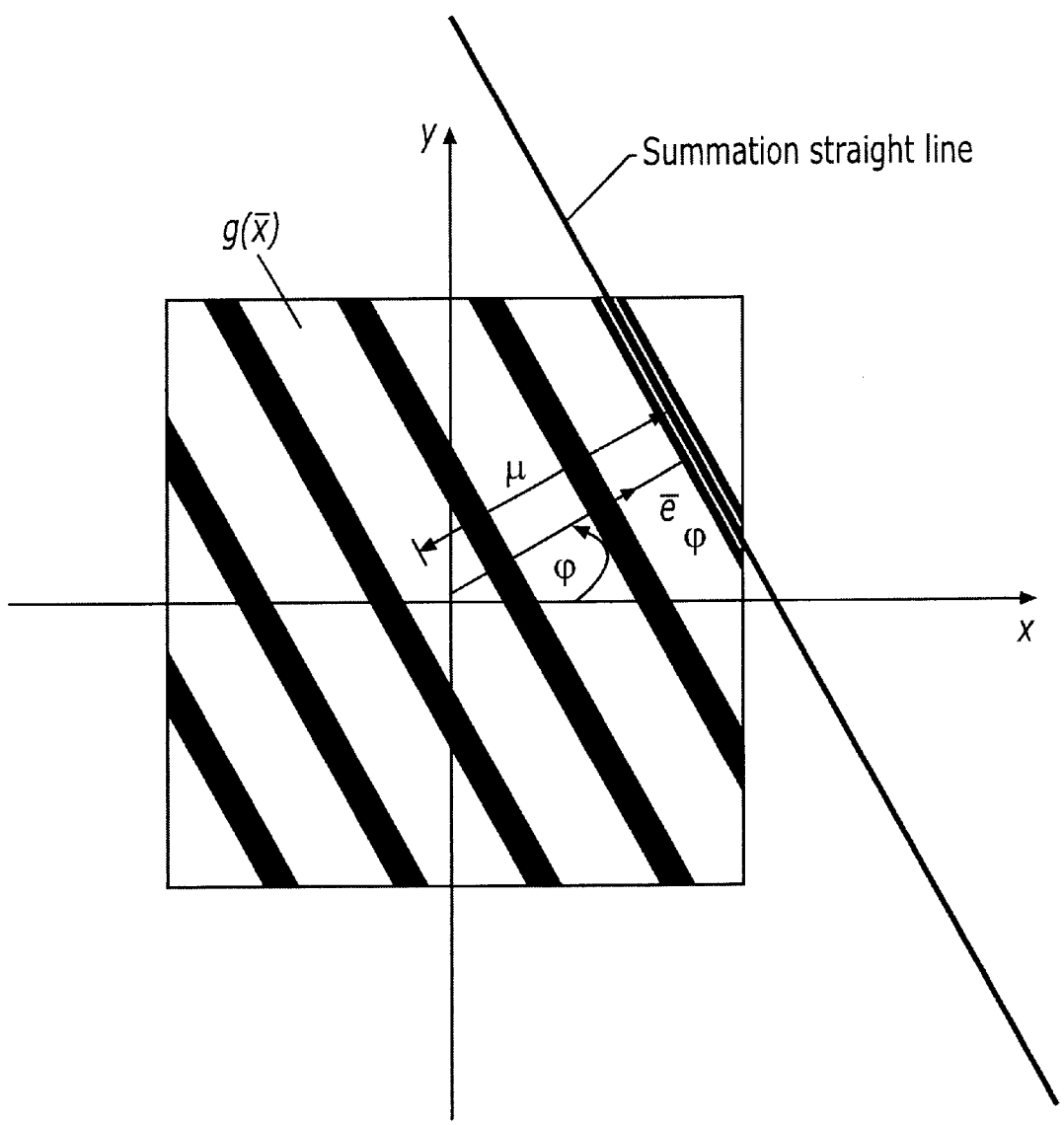
FIG. 2 shows the principle of the Radon transformation.

The value of the Radon transform R for a fixed j and a fixed u is, as shown in FIG. 2, equal to the sum of grey-scale values along a straight line with the Hesse normal form $\vec{x}^T \vec{e}_j - u = 0$. The grey-scale values are summed up along the summation straight line from the origin for each spacing u in conjunction with a constant angle j. In other words, a parallel projection is carried out for each j. The calculated sums are entered into a coordinate system with the abscissa j and the ordinate u. Parallel, straight flutes are concentrated on a strip about an angle $\alpha_j$. Each region about a local summation maximum in the Radon transform characterizes a flute in the grey-scale image.

Figure 3:
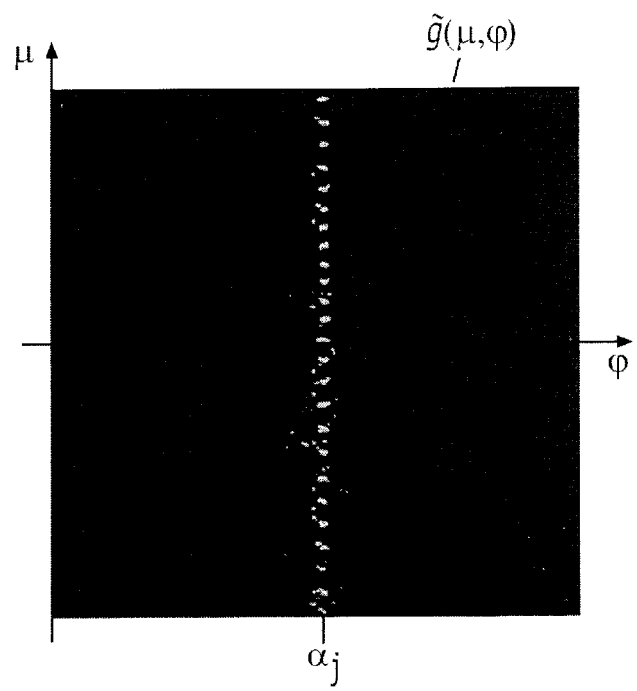
FIG. 3 shows a Radon transform.

Such a Radon transform R is illustrated in FIG. 3. If the square of the Radon transform R is summed in the vertical direction for all j, the result is a maximum for the normal direction $\alpha_j$ of the family of flutes.

$$\alpha_j = \arg\max\{\int \breve{g}^2(\varphi, u) du\}$$

The difference between the angle $\alpha_j$ calculated in such a way and the reference angle g fixed when recording the image gives the desired angle $\alpha^*$ of the helical groove of the ground surface.

The method is fast and depends only on a grey-scale value recording. However, also present is an adjusted image recording device which prescribes the reference direction with a limited accuracy. Apart from this limit, the measuring accuracy of the method also depends on the resolution of the grey-scale image. The available images were recorded by a CCD camera in the format of 512*512 pixels. The Radon transformation is based on the discrete Fourier transformation and the central section theorem. It is not intended to dicuss the theory in more detail here. The calculations for this purpose which were undertaken are so accurate that each pixel of the image to be projected is taken into account. This results in a theoretical maximum angular resolution of approximately 7 min.

However, the inaccuracy of the setting of the reference direction is of precisely the same order of magnitude. The adjustment of the camera can be performed only in accordance with the images produced. Consequently, it is also possible to achieve only an accuracy of one pixel. Either the workpiece itself or its clamping device supplies the reference direction. If, for example, the surface of the investigated workpiece is taken, the tolerance of the machining limits the accuracy. For these reasons, the method described is recommended only for relatively large helix angles in the range of degrees.

The processing of only one image is insufficient for smaller angles. As described above, a plurality of images of the surface affected by helical grooves are recorded at fixed angular spacings in the same image recording set-up. A Radon transform is calculated for each of the images. If one region each is cut out from these about the angle of interest, and a plurality of such sections are assembled in the image sequence, the result is the image illustrated in FIG. 4.

A flute can be tracked in this way over a plurality of images. The helix angle is reproduced in a fashion enlarged corresponding to the image spacings. A precondition for this method is an estimate of the angle $\alpha$ and the periodic length D of the flute profile. $\alpha$ can be estimated for large angles in accordance with the previously described method with an accuracy sufficient to eliminate the strips from the Radon transforms. The periodic length can likewise be determined from the Radon transform, specifically as the mean spacing of the maxima in the u direction for the estimated angle $\alpha_j$:

$$D = \frac{|u(lastmaximum) - u(1stmaximum)|}{n-1},$$

n corresponding to the number of flutes in the image.

The estimated values yield a suitable image spacing A for the image sequence as:

$$A = \frac{\varepsilon D}{2\sin\alpha_j} + \frac{kD}{\sin\alpha_j}$$

$$\varepsilon \in [0;1], k \in Z$$

The flutes can be found uniquely in the Radon plane by using the image spacing A thus chosen: the maximum corresponding to a flute is displaced from one image to the next by at least k and at most k+½ periodic length. This flexible approach for A allows the recording of non-overlapping images in the case of helix angles which are large in relation to the periodic length. This is fixed in a second condition:

A>B  B: image edge length

The image spacing A is related to the further rotation angle $\beta([\beta]=1$ rad) for the workpiece clamping device in the following way:

$$\beta = \frac{A}{R} \quad R: \text{radius of the workpiece}$$

In the above-described estimation method for large helix angles, the greatest inaccuracy results from the adjustment of the camera/workpiece system. It is shown in FIG. 5 that the angular calculation with the aid of the flute tracking method over a plurality of images is independent of a possible angle of rotation y between the workpiece and camera.

However, it is a precondition that the workpiece is clamped such that the workpiece axis and the axis of rotation are aligned. $\alpha$ is then dependent only on the image spacing A and the periodic length D of the flute profile. In FIG. 5a, an axis y indicates the adjusted direction which corresponds to the coordinate system of the camera. An axis r indicates the actual reference direction, and is rotated by an angle γ with respect to the axis y in a negative direction of rotation.

Figure 5:
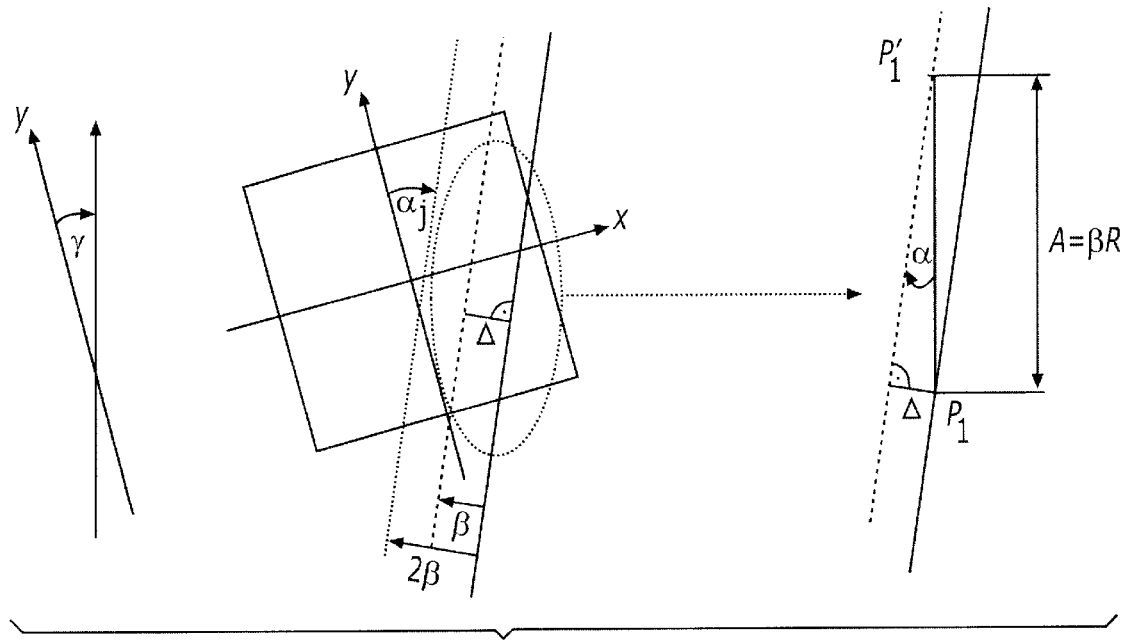
FIG. 5 shows that the determination of the helix angle using the method according to the present invention is independent of any possible rotation of the camera relative to the workpiece.

The angle a illustrated in FIG. 5c is yielded from the difference between the angle $\alpha_j$ and the angle $\gamma$. Using the designations from FIG. 5, it holds that:

$$A = R\beta$$

$$\Delta = D\left(k + \frac{\varepsilon}{2}\right)$$

$$\alpha = \sin^{-1}\left(\frac{\Delta}{A}\right)$$

This estimation rule for $\alpha$ is independent of $\gamma$ and thus of the camera adjustment!

Figure 4:
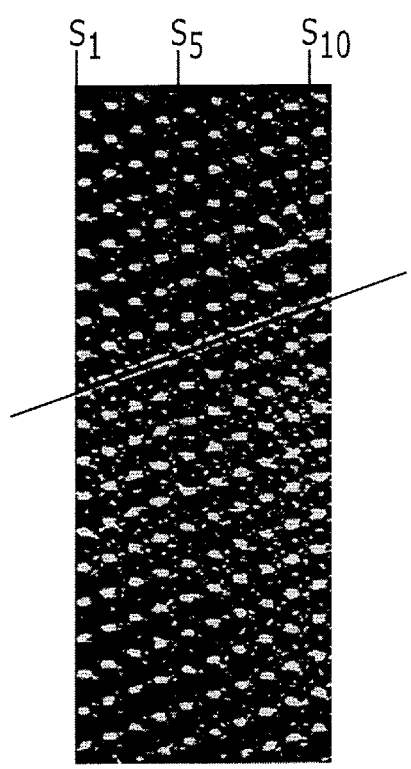
FIG. 4 shows a Radon strip image assembled from ten Radon strips.
Figure 6:
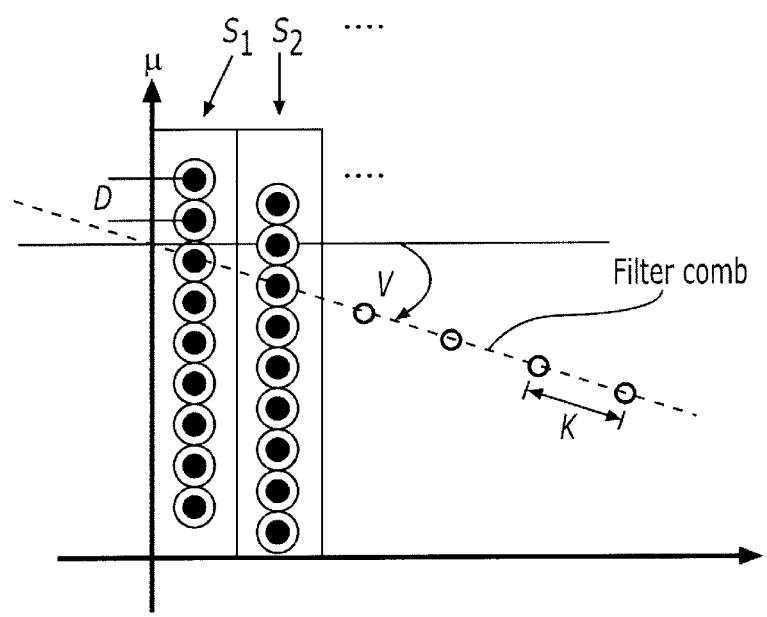
FIG. 6 shows an advantageous structure for a comb filter for processing Radon sectional images.

The assembled Radon sections illustrated in FIG. 4 are now used to obtain exact values for the helix angle and the periodic length. By joining together only the strips from the Radon transforms of the individual images, which surround the estimated angle $\alpha_j$, the angle is virtually enlarged and can thus be measured more accurately. The enlarged angle is denoted by $\Theta$. The periodic length of the flute profile is calculated from the mean spacing of the maxima inside a strip. A comb filter having the structure illustrated in FIG. 6 is constructed using these estimated values. For reasons of clarity, only two Radon transforms $S_1$ and $S_2$ are illustrated in FIG. 6. The filter comb is denoted by F. The parameters $\kappa$ and $\Theta$ are firstly estimated:

$$\hat{\kappa} = \sqrt{\hat{\Delta}^2 + b^2}$$

$$\hat{\vartheta} = \tan^{-1}\left(\frac{\hat{\Delta}}{b}\right) \quad b\text{: width of the Radon sections}$$

where $$\hat{\Delta} = \hat{D}\left(k + \frac{\varepsilon}{2}\right) \quad k, \varepsilon\text{: prescribed}$$

The provisional estimated values for $\hat{\kappa}$ and $\hat{\Theta}$ are used as defining pieces of a comb filter which models the structure of the maxima as in FIG. 6. The Radon sections are multiplied and integrated with the aid of this filter. In this case, the provisional estimated values are slightly varied. As soon as the filter structure and the structure of the maxima coincide exactly, this method supplies an absolute maximum, and the associated geometrical defining pieces can be used as improved estimated values for J and k. From FIGS. 5 and 6, these better values can be calculated back to the desired angle $\alpha$.

$$\hat{\alpha} = \sin^{-1}\left(\frac{\hat{\Delta}}{A}\right)$$

$$\hat{D} = \frac{\hat{\kappa}\sin\hat{\vartheta}}{k + \frac{\varepsilon}{2}}$$

These values $\hat{\alpha}$ and $\hat{D}$ thus estimated are the result of the angular determination for small helix angles. The provisional estimates of the helix angle are improved by the comb filtering over a small range.

Tracking a flute over a plurality of images and thus over a larger area of the surface renders it possible to detect even very small angles in conjunction with identical external conditions. In addition, the statistical reliability of the result is increased. The angle which has been calculated in the investigation of a flute can be verified by taking account of a plurality of flutes.

The accuracy of this second method of angular detection is independent of the camera adjustment. The system is coarsely adjusted, nevertheless, in order to obtain an estimated value for $\alpha$. The exact value is still determined independently thereof, however. It is possible to detect an existing helical groove when the flute in the image last recorded has been displaced by at least one pixel relative to the first image. This smallest angle is a function of the spacing between the first and last image:

$$\alpha_{\min} = \tan^{-1}\left(\frac{1}{zn_A}\right) \quad \begin{array}{l} z\text{: number of images} \\ n_A\text{: number of pixels per image spacing} \end{array}$$

It is therefore possible in principle to measure arbitrarily small angles and to make an appropriately large selection of the spacing. Neither is there a limitation in this case to a circumference of the investigated workpiece, as long as the flute advances continuously.

A method employing a comb filter is firstly described for determining small helix angles. However, this requires estimating the helix angle and the periodic length of the flute profile. The comb filter can then be dimensioned for the purpose of more accurate estimation with the aid of these values.

If there is a low signal-to-noise ratio, the estimation of the periodic length supplies very unreliable values. The reason for this is that, despite the parallel projection of the original image, the stochastic components of the texture in the Radon plane cannot be averaged out, but are still so strong that they can substantially displace the position of the individual maxima in the case of the existing superimposition by the periodic helical groove flutes. This is problematic above all when the flute profile no longer contains one maximum but, owing to the abrasive grain arrangement on the grinding tool, contains a plurality of maxima with similar amplitudes. Determining the periodic time can then still be done only very inaccurately. In conjunction with the likewise unreliable estimate for the helix angle, the result for the comb filter method is a large range over which the filter parameters would have to be varied.

In order to circumvent this problem, the Radon strip image is evaluated with the aid of a correlation analysis (Equ. 1, Equ. 2) (compare FIG. 1). The cross-correlation (KKF) of two functions, in this case these are grey-scale value functions, evaluates the similarity of these functions in dependence on a displacement $\tau$ of the two functions relative to one another:

$$\Phi_{S_1 S_2}(\tau) = \sum_u S_1(u) S_2(u + \tau)$$

$s_i$: strips from the Radon transform of the ith image,
t: displacement coordinate,
u: spacing coordinate of the Radon transform.

The similarity is greatest in the case of the displacement $\tau_{max}$, at which the correlation function has its maximum. Applied to the Radon transforms of two texture images, this means that the displacement of the flutes of an image can be most closely calculated from the displacement coordinate $\tau_{max}$ as long as sections of the same flutes are predominantly contained in the two images.

Figure 7:
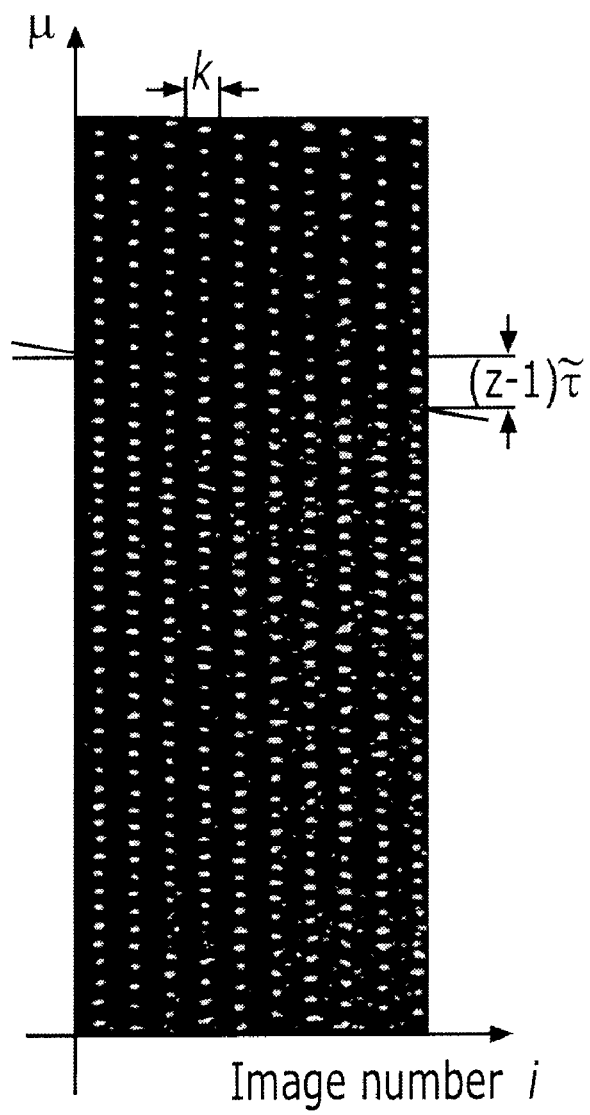
FIG. 7 shows a Radon sectional image, which is used as a basis for a multicross-correlation function.

It is also possible, with the aid of a multicross-correlation function (MKKF) to determine small helix angles which cannot be detected at all or can be detected only unreliably using the method for large angles. The simple cross-correlation function (KKF) of two grey-scale value functions $S_1$ and $S_2$ is expanded in this case by two summations for the purpose of increasing the statistical reliability and the single-valuedness in the case of larger angles. FIG. 7 shows a Radon sectional image which is used as the basis of the multicross-correlation function.

The first sum takes account of the information of all available images of the image sequence. The second summation takes account of the effect that, owing to its width, each flute is projected onto a region about a local summation maximum by virtue of the fact that the strip width k is used to sum up the information of this region in the Radon plane which belongs to the flutes.

MKKF:

$$\Phi_{S_1 \ldots S_z}(\tau) = \sum_{i=1}^{z-1} \sum_{j=1}^{k} \sum_{u} S_i(u,j) S_{i+1}(u+\tau, j) \quad (1)$$

z: number of images in the image sequence
k: width of the Radon strip (in pixels)

An estimated value $\alpha$ of the helix angle which is improved by comparison with $\alpha^*$ is yielded from the argument $\tau$ (compare FIG. 2) of the maximum of this MKKF in accordance with the following equation:

$$\tilde{\alpha} = \tan^{-1}\left(\frac{c\tilde{\tau}}{A}\right)$$

$\alpha$: estimated value of the helix angle,
A: image spacing,
A=R$\beta$
c: edge length of a pixel of the texture image,
R: radius of the workpiece
$\beta$: twisting angle from one image to the next [in rad].

The result of this variant of the method according to the present invention is therefore independent of the camera adjustment (compare FIG. 5) and requires a preceding estimate neither of the helix angle $\alpha$ nor of the periodic length D.

The most accurate estimate of the helix angle is yielded from the cross-correlation function of the Radon strips of the first image of the sequence with the aid of the last permissible image (with index $\zeta$). An image is permissible when it still partially indicates the same flutes as the first, and the displacement of these flutes can therefore be calculated from the correlation function.

$$\Phi_{S_1 S_\zeta}(\tau) = \sum_{u} S_1(u) S_\zeta(u+\tau) \quad (2)$$

The closest maximum is sought starting from the estimated value $\tau$ of the MKKF. The associated displacement argument $\hat{\tau}$ determines the most accurate estimated value $\hat{\alpha}$.

$$\hat{\alpha} = \tan^{-1}\left(\frac{c\hat{\tau}}{(\zeta-1)A}\right)$$

z: index of the last image in the image sequence which still has flutes from the first image.

It is thereby possible also to determine an angle which corresponds to a displacement of the flutes by a pixel from the first to the last permissible image. The resolution is therefore a function of the greatest possible spacing of the two correlated images and thus of the helix angle. The smaller the angle to be measured, the greater the possible image spacing and the better the resolution.

Various disturbing influences appeared in the investigation of specimens. These require different preparations (see FIG. 1) and/or remachining.

In order to compensate the influence of illuminating inhomogeneities on the characteristic of the correlation function, the grey-scale images must be subjected to high-pass filtering. This was performed by means of an exponential filter with the transfer function:

$$1 - \exp\left(-0.347\left(\frac{\sqrt{f_x^2 + f_y^2}}{f_0}\right)^4\right)$$

$f_x, f_y$: spatial frequncies in the $x$-direction and $y$-direction, respectively, $f_0$: cut-off frequency The cut-off frequency was determined interactively, it therefore holding that: $f_0 < D^{-1}$. The coefficient factor $-0.347$ is a constituent of the high-pass routine of the image processing software which was used for filtering.

Because of the very irregular characteristic of the flute profile along a flute, it was still not possible to determine a result in the case of various specimens. The KKF does show a clearly periodic structure, but the height of the maxima fluctuates very strongly owing to disturbances, with the result that the principal maximum does not occur in every case for the true helix angle. This ambiguity can be resolved with the aid of the method for large angles by using the estimated value $\alpha^*$ obtained there for the helix angle to limit the $\tau$ region considered in the MKKF (compare the dashed arrow in FIG. 1). The method for large angles then supplies the statement as to which maximum is the correct one, and the second method contributes the exact location of the maximum in relation to the estimated helix angle.

A unique solution results when there is still only one maximum remaining as possible solution. This is the case when the limits of the possible angular range around the first estimated value obey the following relationship:

$$A \times (\tan \alpha_{go} - \tan \alpha_{gu}) < D,$$

$\alpha_{go}, \alpha_{gu}$: upper and lower limits, respectively, of the possible angular range, D: periodic length of the flute texture.

That is to say that the region of the possible displacement of the flutes is smaller than one periodic length. The angular interval $[\alpha_{go}, \alpha_{gu}]$ is yielded from the unreliability of the first estimate $\alpha^*$ and the adjustment error with reference to the angle between the camera coordinate system and workpiece axis.

The accurate estimated value $\hat{\alpha}$ of the helix angle is yielded from the argument of the maximum of the KKF determined in this way.

What is decisive for the accuracy of the angular calculation is the determination of the magnitude of a pixel, that is to say the constant c, which is required in order to convert the spacing between successive images into a number of pixels. In the present case, a variable enlargement was used and the constant was determined for each image series using a simple principle. A material measure, for example millimetre-square graph paper, is fastened on the specimen, and a grey-scale image is recorded at the desired enlargement. The spacing of the millimetre lines can be determined in pixels with the aid of the Radon transform, and converted directly into the constant.

Further errors can arise owing to tilting, that is to say clamping the workpiece in a fashion which is not exactly aligned. A flute is then not projected exactly onto a line in the Radon strip image, but a sinusoidal function is superimposed. The spacing coordinate u of a flute in the Radon strip image then obeys the following equation:

$$\tilde{u}(i) = R \cdot \sin \psi \sin(i\beta + \beta_o) + [i\beta \tan \alpha + u_1]$$

R: radius of the workpiece,
Ψ: angle of tilting,
β: twisting angle from one image to the next,
$\beta_0$: angle of the initial position,
α: helix angle,
$u_1$: position of the flute in the first image.

The straight line equation of the helical groove of interest (in square brackets) can be extracted by suppressing the periodic component of known periodic length, and the helix angle can then be estimated.

Figure 8:
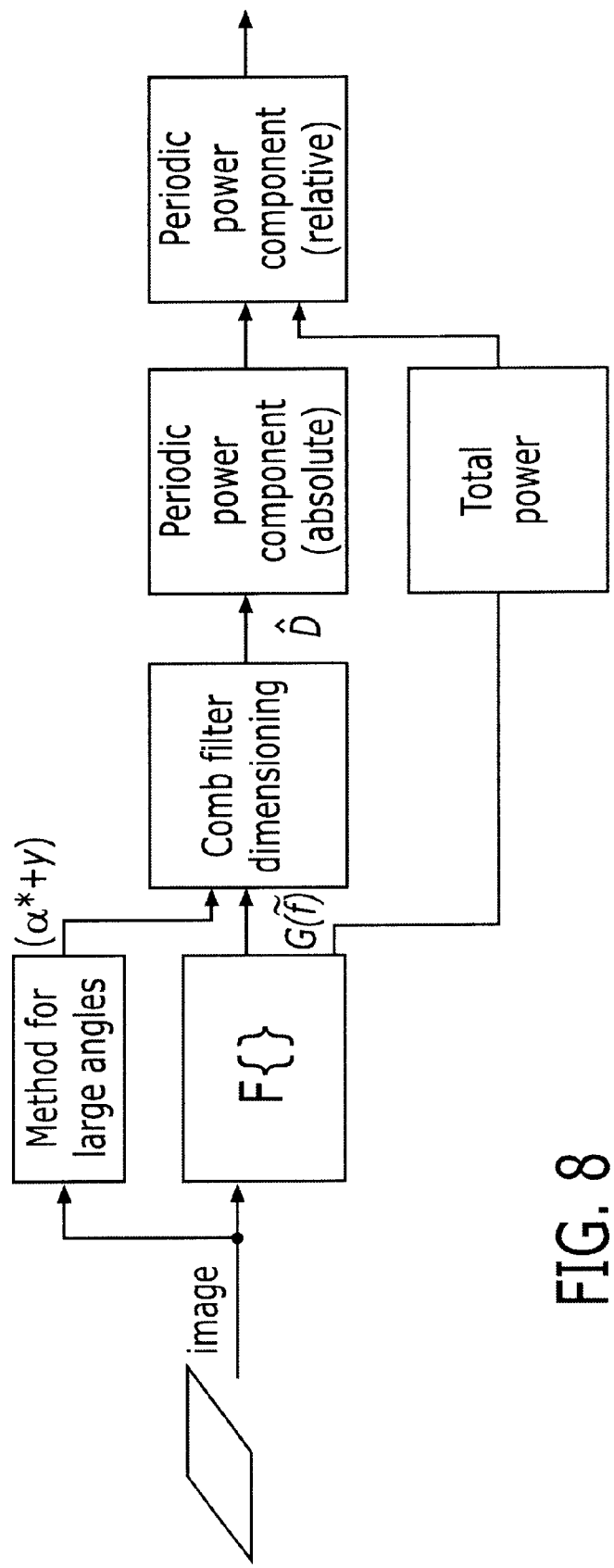
FIG. 8 shows a schematic illustration of the calculation of the helical groove salience from the power components.

In addition to the exact estimation of the helix angle, the characterization of the helical groove phenomenon requires an estimate of the salience (relative strength) of the helical groove. This requires a more accurate definition of the term "salience". A functionally relevant quantification of the helical groove salience would require the densities of the specimens or an equivalent expert judgement also to be incorporated into the definition of a measure of the salience. Since neither one nor the other was to hand at the time of this study, an approach was formulated from considerations in signal theory which compares the power components of the periodic flutes and the overall texture. The overall sequence of this approach is illustrated in FIG. 8.

The Fourier transform $G(\vec{f})$ is formed from an image of the flute texture. Periodic components of the workpiece surface are concentrated in the Fourier plane onto their fundamental frequency $D^{-1}$ and their higher harmonics, specifically on a line perpendicular to the angle (α+γ) at which the flutes appear in the original image. If the square of the absolute value of the Fourier transform is formed, the result is the periodogram (as estimator for the power density spectrum). The absolute periodic power component is extracted therefrom with the aid of a comb filter K(θ,d). A comparison of the absolute periodic power component with the total power P gives the relative periodic power component.

Figure 9:
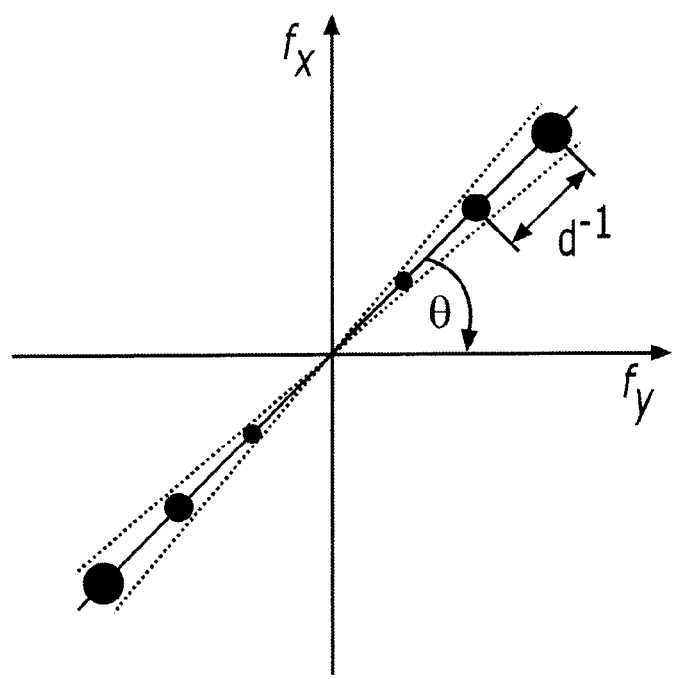
FIG. 9 shows the circular passbands of a comb filter for extracting the periodic power component.

The passbands of a comb filter with the parameters θ and d are illustrated in FIG. 9. The angle parameter θ of the comb filter is determined with the aid of the method for large angles (see FIG. 8) to be q=(α*+γ). This need not be an image of the adjusted workpiece/camera system, since the periodic length and the amplitude of the helical groove are determined independently of the helix angle. The method for large angles is required only in order to determine the angular position of the periodic components in the Fourier plane, in which case α and γ need not be explicitly determined. The second parameter d determines the spacing of the two openings of the filter. This is determined by the argument of the maximum of the integral over the product of the periodogram and filter function K(θ,d). The associated value d=$\hat{D}$ is an estimated value of the periodic length D, because the product becomes a maximum when the filter openings and the periodic components coincide.

$$\hat{D} = \arg\max_d \left[ \int_{-\infty}^{\infty} |G(\vec{f})|^2 K(\theta, d) d\vec{f} \right]$$

$\hat{D}$: Estimated value of the periodic length of the helical flutes
G: Fourier transform of the texture image
K(θ,d): comb filter function
d: spacing parameter of the filter openings
θ: estimated value of the angle at which the flutes appear in the image The comb filter transfer function K(θ,d) is used to attempt to "match" the helical groove structure geometrically in the frequency band. If the parameters of the filter and the helical groove correspond, that is to say the two structures coincide, a maximum is to be expected for the signal power at the output of the comb filter. In order to take account of the unreliability of the angular estimate (α*+γ), an appropriate angular range is covered by the filter. Fluctuations in the periodic length of the helical groove structure require a minimum size of the filter openings. The periodic component of the power density is extracted with the aid of the comb filter dimensioned in this way. The measure of the helical groove salience is defined as:

$$\frac{\int_{-\infty}^{\infty}\int_{-\infty}^{\infty} |G(\vec{f})|^2 K(\hat{D}, \theta) d\vec{f}}{\int_{-\infty}^{\infty}\int_{-\infty}^{\infty} |G(\vec{f})|^2 d\vec{f}}$$

What is claimed is:

1. A method for operating a camera to determine a structure of machining marks on a surface of a cylindrically finely finished workpiece, the camera and the workpiece being mutually aligned, the method comprising the steps of:
   recording an image of surface characteristics of the workpiece; and
   in order to determine a helically running structure of the machining marks, performing the steps of:
      performing a Radon transformation of the image, and determining a helix angle of those of the machining marks that are helical;
      rotating the workpiece;
      recording a plurality of images if the surface characteristics of the workpiece at a constant twisting angle;
      providing a plurality of Radon transforms by performing the Radon transformation for each one of the plurality of images;
      extracting a Radon strip from each one of the plurality of Radon transforms;
      juxtaposing the Radon strips of the Radon transforms of each one of the plurality of images in a Radon strip image; and
      performing a correlation analysis of the juxtaposed Radon strips.

2. The method according to claim 1, further comprising the step of:
   providing a scale at a level of the surface of the workpiece.

3. The method according to claim 1, further comprising:
   illuminating the surface of the workpiece to generate a high contrast between flute peaks and troughs of the surface of the workpiece.

4. The method according to claim 1, further comprising:
choosing an image section for recording.

5. The method according to claim 4, wherein the image section includes a number of flutes, the number selected to be within a range between 5 and 50.

6. The method according to claim 1, wherein the image is an enlarged grey-scale image.

7. The method according to claim 1, wherein the image is recorded via a macrolens.

8. The method according to claim 1, wherein the determining of the helix angle further comprises:
calculating a difference between a first angle and a second angle.

9. The method according to claim 8, further comprising:
determining from the Radon transformation, an angular position of flutes of the surface of the workpiece, wherein the first angle is a defined angle of the camera relative to the workpiece, and the second angle is the angular position of the flutes.

10. The method according to claim 5, wherein the plurality of images are recorded at fixed angular spacings.

11. The method according to claim 5, wherein the plurality of images are non-overlapping images.

12. The method according to claim 5, wherein the helix angle is a small helix angle.

13. A method for operating a camera to determine a structure of machining marks on a surface of a cylindrically finely finished workpiece, the camera and the workpiece being mutually aligned, the method comprising:
rotating the workpiece;
recording a plurality of images of surface characteristics of the workpiece at a constant twisting angle;
to determine a helically running structure of the machining marks, performing the following:
providing a plurality of Radon transforms by performing a Radon transformation for each one of the plurality of images;
extracting a Radon strip from each one of the plurality of Radon transforms;
juxtaposing the Radon strips of the Radon transforms of each one of the plurality of images in a Radon strip image;
performing a correlation analysis of the juxtaposed Radon strips; and
determining a helix angle of those of the machining marks that are helical;
independently of the Radon transformation, producing a Fourier transform of at least one of the plurality of images;
forming a periodogram from the Fourier transform;
filtering the periodogram in accordance with an operation of a comb filter;
determining a spacing parameter of the comb filter in conjunction with a maximization of a periodic power component;
calculating the periodic power component as a ratio of a proportion of the machining marks to the surface, wherein the spacing parameter of the comb filter corresponds to an estimated value of a periodic length of a helical groove structure; and
calculating a number of threads of the helical groove structure from the helix angle and the periodic length.

14. The method according to claim 13, wherein the periodogram is formed by squaring the Fourier transform's absolute value.

* * * * *

UNITED STATES PATENT AND TRADEMARK OFFICE
CERTIFICATE OF CORRECTION

PATENT NO. : 6,873,721 B1
DATED : March 29, 2005
INVENTOR(S) : Beyerer et al.

It is certified that error appears in the above-identified patent and that said Letters Patent is hereby corrected as shown below:

Title page, Item [54] and Column 1, line 1,
Title, change "METHOD AND DEVICE FOR DETERMINING AN ANGLED STRUCTURE IN THE SURFACE OF A PRECISION MACHINED CYLINDRICAL WORK PIECE" to -- METHOD AND DEVICE FOR DETERMINING A HELICAL GROOVE STRUCTURE IN THE SURFACE OF A FINELY FINISHED CYLINDRICAL WORKPIECE --;

Column 2,
Line 1, change "standarized" to -- standardized --;

Column 5,
Line 26, change "projected,onto" to -- projected onto --;
Line 67, change "quantative" to -- quantitative --;

Column 7,
Line 13, change "elix angle" to -- helix angle --;
Line 55, change "dicuss" to -- discuss --;

Column 9,
Line 12, change "adjustment!" to -- adjustment. --;

Column 15,
Lines 21, 23 and 25, change "claim 5" to -- claim 1 --.

Signed and Sealed this

Third Day of January, 2006

JON W. DUDAS
*Director of the United States Patent and Trademark Office*